(12) United States Patent
Wolfe et al.

(10) Patent No.: US 7,918,894 B2
(45) Date of Patent: Apr. 5, 2011

(54) KINEMATIC TOTAL WRIST ARTHROPLASTY

(75) Inventors: Scott W. Wolfe, Greenwich, CT (US); Joseph John Crisco, III, Barrington, RI (US)

(73) Assignees: New York Society for the Ruptured and Crippled Maintaining the Hospital for Special Surgery, New York, NY (US); Rhode Island Hospital, Providence, RI (US)

( * ) Notice: Subject to any disclaimer, the term of this patent is extended or adjusted under 35 U.S.C. 154(b) by 0 days.

(21) Appl. No.: 12/424,006

(22) Filed: Apr. 15, 2009

(65) Prior Publication Data

US 2009/0204223 A1    Aug. 13, 2009

Related U.S. Application Data

(63) Continuation of application No. 11/843,502, filed on Aug. 22, 2007, now abandoned.

(60) Provisional application No. 60/839,726, filed on Aug. 22, 2006, provisional application No. 60/871,400, filed on Dec. 21, 2006, provisional application No. 60/917,785, filed on May 14, 2007.

(51) Int. Cl.
    *A61F 2/42* (2006.01)
(52) U.S. Cl. ................... 623/21.14; 623/21.12
(58) Field of Classification Search ..... 623/21.11–21.19
    See application file for complete search history.

(56) References Cited

U.S. PATENT DOCUMENTS

| 4,040,130 | A | | 8/1977 | Laure | |
|---|---|---|---|---|---|
| 4,180,871 | A | * | 1/1980 | Hamas | ...................... 623/21.13 |
| 4,229,840 | A | * | 10/1980 | Gristina | ...................... 623/21.13 |
| 4,242,759 | A | | 1/1981 | White et al. | |
| 6,059,832 | A | | 5/2000 | Menon | |
| 6,485,520 | B1 | | 11/2002 | Hubach et al. | |
| 6,746,486 | B1 | * | 6/2004 | Shultz et al. | ............... 623/21.12 |
| 2006/0036330 | A1 | | 2/2006 | Shultz et al. | |

FOREIGN PATENT DOCUMENTS

| DE | 10237016 | 2/2004 |
|---|---|---|
| GB | 2269752 | 2/1994 |

OTHER PUBLICATIONS

Rahimtoola et al., Total modular wrist prosthesis a new design, Scandinavian journal of plastic reconstructive surgery and hand surgery/NOrdisk plastikkirurgi. 38, pp. 16-165, Feb. 2003.

Crisco, J. et al., In vivo Radiocarpal Kinematics and the Dart Thrower's Motion, The Journal of Bone & Joint Surgery, 87, pp. 2729-2740, 2005.

Wolfe, Scott et al., The Dart-Throwing Motion of the Wrist: Is it Unique to Humans?, The Journal of Hand Surgery, vol. 31A, No. 9, pp. 1429-1437, Nov. 2006.

(Continued)

*Primary Examiner* — Bruce E Snow
(74) *Attorney, Agent, or Firm* — Fish & Richardson P.C.

(57) ABSTRACT

An implant system and apparatus configured to permit motion of the wrist in at least one physiological direction, as well as in a dart thrower's motion, and constrain motion of the wrist in at least one non-physiological direction are provided. The implant according to one embodiment includes a distal component and proximal component. Each of the distal and proximal components includes a primary articulating portion and a secondary articulating portion. Primary and secondary articulating portions include at least one component having either a substantially convex or a substantially concave shape. The secondary articulating portion is configured to be radially and volarly disposed in relation to the primary articulating portion.

24 Claims, 10 Drawing Sheets

OTHER PUBLICATIONS

Product Comparison, Total Wrist Systems, SBI website, Jun. 2006.
SBi Total Wrist Artrhoplasty Educational Didactic and Lab for the New SBi Total Wrist Implant System, Workshop Held Sep. 14, 2008 by Melvin Rosenwasser and William Cooney.
MAESTRO wrist reconstructive system, Biomet Orthopedics, Inc., 2005.
Letter dated Jun. 18, 2010 sent on behalf of Ms. Alyssa Ricker in reference to U.S. Appl. Nos. 12/424,006 and 12/435,140.

* cited by examiner

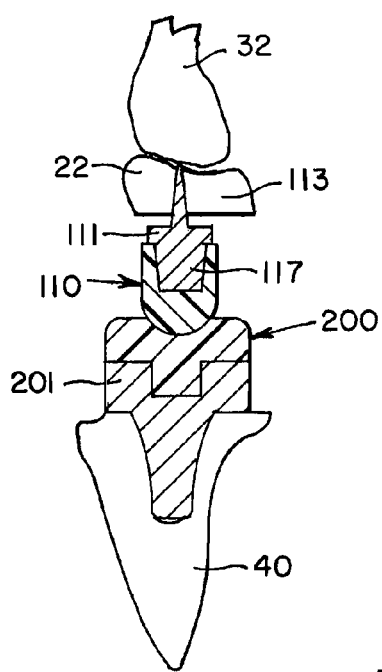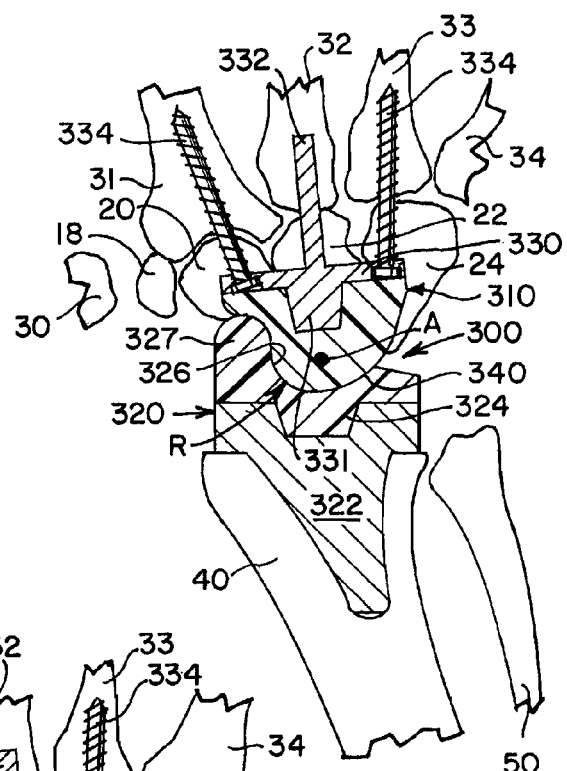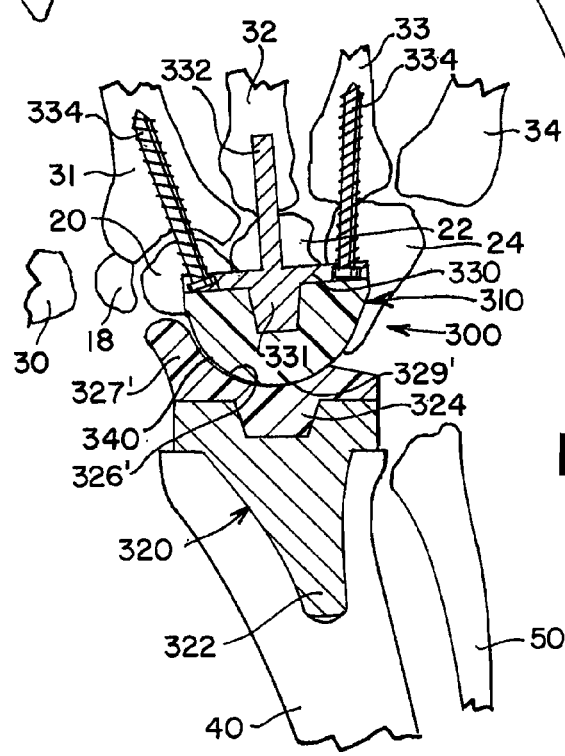

FIG. 11A
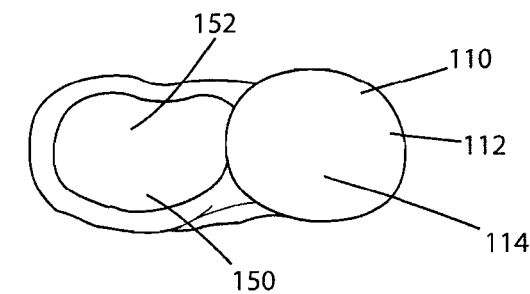
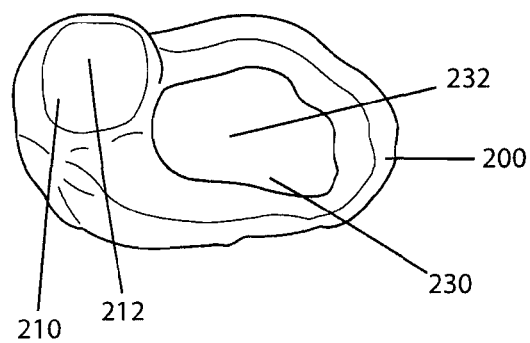
FIG. 11B
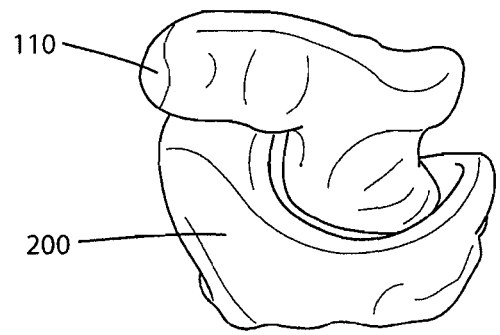
FIG. 11C
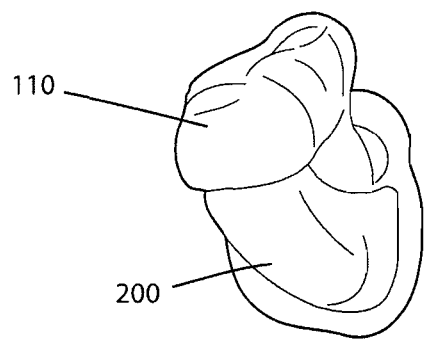

KINEMATIC TOTAL WRIST ARTHROPLASTY

CROSS-REFERENCE TO RELATED APPLICATIONS

This application is a continuation of U.S. patent application No. 11/843,502, filed Aug. 22, 2007, which claims priority to U.S. Provisional Patent Application No. 60/839,726, filed Aug. 22, 2006; U.S. provisional patent application No. 60/871,400, filed Dec. 21, 2006; and U.S. provisional patent application No. 60/917,785, filed May 14, 2007, the disclosures of which are hereby incorporated by reference in their entirety.

GOVERNMENT SUPPORT

Work described herein was supported in part by NIH grant AR44005-NIH. The U.S. government therefore may have certain rights in the invention.

TECHNICAL FIELD

The present invention relates to medical implants and procedures, and more particularly, relates to a wrist implant that permits physiological motion of the joint and constrains non-physiological motion of the joint.

BACKGROUND

The human hand consists of several small bones called phalanges and metacarpals. The forearm consists of two bones, namely, the radius and the ulna. The wrist is broadly defined as the multiple articulations of the eight carpal bones (carpus) with the neighboring hand and forearm. This complex system of articulations works in unison to provide a global range of motion for the wrist joint. Motion at the wrist joint occurs between the radius and the first (or proximal) row of carpal bones, which move essentially as a single functional unit, and between the proximal carpal row and the distal carpal row of carpal bones. There is minimal motion between the bones of the distal carpal row and the metacarpal bones of the hand.

As illustrated in FIG. 1, there are eight carpal bones, namely, the scaphoid 10, lunate 12, triquetrum 14, pisiform 16, trapezium 18, trapezoid 20, capitate 22 and the hamate 24. Each carpal bone possesses a unique, highly complex three-dimensional shape. The majority of their outer surfaces consist of two types of tissue: a cartilaginous tissue permitting articulations with other bones, and fibrous tissues permitting insertions of ligaments. The arrangement of the eight carpal bones can be grossly described as consisting of two rows to form a compact, powerful unit. The proximal carpal row contains the scaphoid 10 (also called the navicular), lunate 12, and triquetrum 14. These three bones articulate proximally with the radius 40 and the triangular fibrocartilage. The ulna 50 does not articulate directly with the carpus but is separated from the triquetrum 14 by the triangular fibrocartilage, which acts as a stabilizing structure. The distal carpal row contains the trapezium 18, trapezoid 20, capitate 22, and hamate 24 and articulates distally with the five metacarpals (metacarpals bones 30, 31, 32, 33 and 34), and proximally with the three bones of the proximal carpal row. The pisiform 16 is a sesamoid bone which articulates with the triquetrum alone, and does not participate directly in carpal or global wrist motion. The scaphoid 10 acts as a connecting link between the proximal and distal carpal rows and is a critical coordinator of carpal motion.

The wrist is generally divided into five primary articulations in addition to the intercarpal joint spaces: the radiocarpal joint, the midcarpal joint (between the proximal and distal carpal rows), the large carpometacarpal joint (between the distal carpal row and the second, third, fourth and fifth metacarpals (bones 31, 32, 33 and 34), the thumb carpometacarpal joint (between the first metacarpal 30 and the trapezium 18) and the distal radio-ulnar joint (DRUJ). The midcarpal joint is the joint between the scaphoid, lunate, and triquetrum proximally, and the second row of carpal bones distally and is made up of three distinct portions: in the center the head of the capitate and the superior surface of the hamate articulate with the deep cup-shaped cavity formed by the navicular and lunate, and constitute a sort of ball-and-socket joint. On the radial side of the midcarpal joint, the trapezoid and trapezium form a concave articulating surface with the distal scaphoid. On the ulnar side, the convex hamate surface articulates with a helicoidal surface of the distal triquetrum. The midcarpal joint can thus be characterized as containing a number of convex and concave surfaces that interact with one another to provide the desired joint movements.

Radiocarpal ligaments limit motion between the radius and the carpal bones and intercarpal ligaments limit motion between neighboring carpal bones. The distal radioulnar joint is an articulation between the radius and the ulnar head, and is contained within a capsule-like structure of cartilage, synovial membrane and ligaments. A triangular fibrocartilage between the radius 40 and the carpus separates the distal radioulnar joint from the rest of the wrist.

The hand and wrist are involved in virtually every human functional activity and as such, are vulnerable to a high number of traumatic injuries, primary osteo-arthritis, and secondary degenerative disease. Examples of traumatic injuries include a break (fracture) of a carpal bone, a dislocation of all or part of the carpus, or a ligament injury between one or more of the carpal bones. Osteo-arthritis, also known as degenerative joint disease, is a process of progressive deterioration of articular cartilage and formation of new bone (osteophytes) at the joint surface. Primary osteo-arthritis is age related and associated with repetitive and/or high mechanical stress on a normal joint. Secondary osteo-arthritis is due to an underlying cause, such as trauma, inflammatory, metabolic, developmental, or connective tissue diseases. Importantly, untreated traumatic injuries of the carpus (e.g. scaphoid fractures, scapho-lunate ligament injuries) are the most frequent cause of secondary osteo-arthritis of the wrist.

There are a number of different techniques and surgical procedures for remedying either an injury and/or the effects of wrist degeneration. For example, a total joint arthroplasty is a surgical procedure that replaces the entire joint with an artificial implant (artificial joint). Wrist arthodesis (i.e., a partial or complete surgical fusion of the wrist) is typically favored by most surgeons over wrist arthroplasty for active patients, despite the limitations of motion and function associated with wrist fusion. This is due in large part to the uncertain outcome of wrist arthroplasty, which may result from implant wear, loosening and failure. Each of these procedures and the existing wrist arthroplasty devices has limitations and/or deficiencies.

The design of wrist prostheses has evolved based on clinical experience, and kinematic and biomechanical studies. This evolution (which spans more than 30 years) has generally yielded three distinct generations of total wrist arthroplasty implants. The first generation was a one-piece silicone design that had no articulating components and was made from a high-performance elastomer. The second generation used two articulating components, usually with a metal-on-polyethylene bearing, and cemented fixation into the metacarpal canals distally and the radius proximally. The third generation implants included the Biaxial, Trispherical, and other types of prostheses. These designs attempted to improve wrist balance and prosthetic durability.

Continued problems with distal component loosening and wrist imbalance with these prostheses prompted development of a total wrist implant called the Universal by Kinetikos Medical, Inc. of San Diego, Calif. This particular prosthesis has a different method of fixation for the distal component in that it is fixed by a short central stem cemented into the capitate, and features two deep threaded osteointegrated screws are fixed into the radio and ulnar aspects of the carpus. This fixation is combined with a partial intercarpal arthrodesis to provide the potential for long-term implant survival. While this type of implant, as well as other new designs, has had some success in some patients, they continue to have problems with loosening of prosthetic fixation, and instability. Current prosthetic designs typically replace the radiocarpal joint surface rather than the midcarpal joint surface, and as such, may restrict certain highly important functional motions of the wrist.

The radial and carpal base components of current prostheses are generally made of CoCr and Ti, respectively. In these systems, the radial component is inclined 20 degrees to replicate the inclination of the articular surface of the normal distal radius. A convex ultra-high molecular weight polyethylene component fixed to the carpal base provides the distal articular surface. The shape of this component is generally elliptical. These articulating surfaces of the carpal and radial components create a dual-axis articulation that is best suited for planar motions of radial and ulnar deviation or flexion and extension. In other words, true congruency is maintained in only uniplanar rotations. If the wrist is moving through radio-ulnar deviation for instance, conjoined motions of flexion or extension will cause partial liftoff of the component, articular incongruency, uneven articular wear, implant fixation stress, and potential implant instability. A similar situation exists with planar motion in flexion-extension, wherein conjoined motion of radio-ulnar deviation will cause similar incongruency of the components. The articular concavity of the radial component (toroidal shaped) has been described as deep enough to provide immediate stability when the components are inserted under appropriate tension. Soft tissue balancing can be adjusted by varying the polyethylene thickness to limit component instability. Although conventional prosthetic designs have improved the problems associated with loosening of the distal component, their design does not fully address this problem, and other problems, including dislocation, wear, and instability.

Most sporting activities, occupational activities and many activities of daily living utilize non-planar motions of the wrist (i.e., neither pure flexion-extension or pure radio-ulnar deviation). The "dart-thrower's arc" of wrist motion is defined as a coupled or conjoined motion of flexion-extension and simultaneous radio-ulnar deviation. In throwing for instance, the hand and digits grip an object (rock, baseball, dart, javelin) and the wrist is simultaneously cocked into extension and radial deviation, which initiates the activity. The shoulder and elbow are activated to raise the object overhead. During the throwing portion, the shoulder, elbow, forearm and wrist participate to deliver the object in a smooth, accurate and coordinated sequence of radial extension to ulnar flexion. To maximally accelerate the object, the follow-through portion of wrist motion terminates with the hand in a coupled position of flexion and ulnar deviation. Procedures or diseases which impair this arc have been demonstrated to cause marked functional impairment. Recent kinematic evidence has shown a remarkable degree of uniformity of carpal motion within the dart-thrower's motion (DTM), and near absence of motion in the entire proximal row of carpal bones. The dart-thrower's arc of motion occurs almost exclusively at the midcarpal joint (the joint between the distal carpal row (triquetrum, trapezoid, capitate and hamate) and the proximal carpal row (scaphoid, lunate and trapezium). The human midcarpal joint has a unique convex and concave surface that differs distinctly from other primate midcarpal joints. Anthropologic evidence suggests that the dart-thrower's arc may be unique to humans and may have provided an evolutionary advantage for hunting, combat, and protection of offspring. Ongoing 3D motion analysis studies are demonstrating the precise motion paths of the wrist during occupational and sporting activities in normal and injured patients and will provide data to help better design rehabilitation protocols and devices to optimize this motion.

It should be emphasized that there may be different proportions of flexion-extension and radial-ulnar deviation for different activities; thus there may be several unique "dart-thrower's arcs" of wrist motion. Most functional activities begin with 10-30 degrees of wrist extension and 10-30 degrees of radial deviation, and finish in 10-40 degrees of ulnar deviation and 10-40 degrees of wrist flexion. All share in common, however, a smooth coupling of motion that progresses from some amount of wrist extension and radial deviation to some amount of wrist flexion and ulnar deviation. There are some activities (e.g. Frisbee throwing) that require a reverse dart-thrower's motion (from ulnar deviation and wrist flexion to radial deviation and wrist extension), such that the direction of motion is opposite to the dart-thrower's motion, but the coupled motion path is the same, and unique to the orthogonal axes of wrist flexion-extension and radial-ulnar deviation. Importantly, there are no functional activities that have been demonstrated to use an inverse dart-thrower's motion (i.e., from radial flexion to ulnar extension or vice-versa).

Conventional arthroplasty devices are incapable of providing and/or perfecting the above-described dart thrower's motion that is critical to performing a significant number of everyday activities.

Referring now to FIG. 2 in which x, y and z axes and motions of rotation described as radial/ulnar deviation, flexion/extension, and supination/pronation are illustrated. As shown, radial/ulnar deviation is performed about the y-axis. Rotation about the positive y-axis is defined to be radial deviation. The flexion/extension motion is performed about the x-axis, with flexion in the positive x direction. Supination/pronation, which physiologically occurs primarily between the radius and ulna, can also be described relative to the coordinate system in FIG. 2 as rotation about the z-axis, with supination in the positive z direction. Accordingly, translational motion can be described using this same coordinate system. Dorsal/ventral translation occurs along the y-axis, with dorsal being in the positive y direction. Radial/ulnar translation occurs along the x-axis, with radial translation being positive. Distal/proximal translation occurs along the z-axis, with distal translation being in the positive z direction. It should be noted that these well accepted descriptions of wrist motion direction of are based on anatomical planes, which are not necessarily the planes of motion that are the most functional or the most common. These anatomically defined motions of radial/ulnar deviation and flexion/extension are orthogonal to each other. The dart thrower's motion, which is wrist motion oblique to the orthogonal coordinate axes in FIG. 2 and consists of an arc of motion that includes combined radial extension to and from ulnar flexion, is an important functional motion of the wrist. In other words, considering the rotation axis of flexion/extension is the x axis, and the rotation axis of radial/ulnar deviation is the y axis, the rotation axis of the dart throwers' motion contains components of both the x axis and the y axis. The dart thrower's motion is used to describe any wrist motion that includes components of both flexion/extension and radial/ulnar deviation.

SUMMARY

According to some embodiments, the present invention is a wrist implant that includes a distal component and a proximal component. Each one of the distal and proximal components can be configured to have two articulating portions. Each of the components includes one articulating portion having a substantially concave shape and one articulating portion having a substantially convex shape. One articulating portion is configured to be radially and volarly disposed in relation to the other articulating portion. The two articulating portions can be configured as "double ball and socket" and arranged to mimic a normal midcarpal joint according to at least one embodiment.

In some embodiments, the articulating portions of each one of the components can be configured to be continuous with respect to one another. This means that the surface of the convex articulating portion is continuous with the surface of the concave articulating portion, and vice versa. In other embodiments, the surfaces can be partially continuous with one another. This means that at least one section of the surface of the convex articulating portion is continuous with at least one section of the surface of the concave articulating portion, and vice versa.

In an alternate embodiment, the present invention relates to a wrist implant system having a first portion configured to have a first protrusion and a first recessed portion and a second portion configured to have a second protrusion and a second recessed portion. The first recessed portion has a concave shape configured to accommodate placement of the second protrusion having a convex shape. The second recessed portion has a concave shape configured to accommodate placement of the first protrusion having a convex shape. The first and second portions are configured to permit motion of the wrist in at least one physiological direction and constrain motion of the wrist in at least one non-physiological direction.

In another embodiment, the wrist implant system has a radial portion that is configured to have a smooth, undulating articulating surface that has both concave and convex components that articulate with the distal, reciprocally designed articulating surface of the carpal component. The shape of the design mimics the normal midcarpal articulation.

The first and second portions of each embodiment are further configured to permit motion of the wrist in at least one physiological direction and constrain motion of the wrist in at least one non-physiological direction. In some embodiments, the wrist implant system of the present invention can be configured to permit its user a range of motions. Such motions, include a dart thrower's motion ("DTM"), flexion/extension, radial/ulnar deviation, and/or other motions, as well as any combinations of the above motions. In some embodiments, the present invention can be configured to limit radial deviation, as well as constrain supination and pronation of the wrist.

According to yet another embodiment, a surgeon may elect to perform a hemi-arthroplasty of the wrist instead of a total wrist arthroplasty, and in doing so, replace only the proximal carpal row of the wrist, leaving the native distal row and normal cartilage intact. The hemi-arthroplasty implant for the wrist is constructed to be installed by replacing the proximal carpal row and the distal radius articular surface, while at the same time, preserving the distal carpal row and the distal radio-ulnar joint. The hemi-arthroplasty implant includes a prosthesis that has a stem that is implanted in the radius and has a modular bearing surface that articulates with the healthy distal carpal bones. The native capitate and hamate bones are preserved and articulate with the modular bearing surface, thereby resembling the native midcarpal joint. The modular bearing surface is configured to preserve the shape of the midcarpal joint and allow for the "dart-thrower's functional arc of motion." It will therefore be understood that in each of the embodiments of the present invention, the wrist implant is configured to permit normal wrist motion and is particularly configured to permit the various dart thrower's motion, which are various combinations of radial extension and ulnar flexion.

Other features and advantages of the present invention will be apparent from the following detailed description when read in conjunction with the accompanying drawings.

BRIEF DESCRIPTION OF THE DRAWING FIGURES

The foregoing and other features of the present invention will be more readily apparent from the following detailed description and drawings figures of illustrative embodiments of the invention in which:

FIG. 10 is a cross-sectional view taken along the line 10-10 of FIG. 9;

Figure 14:
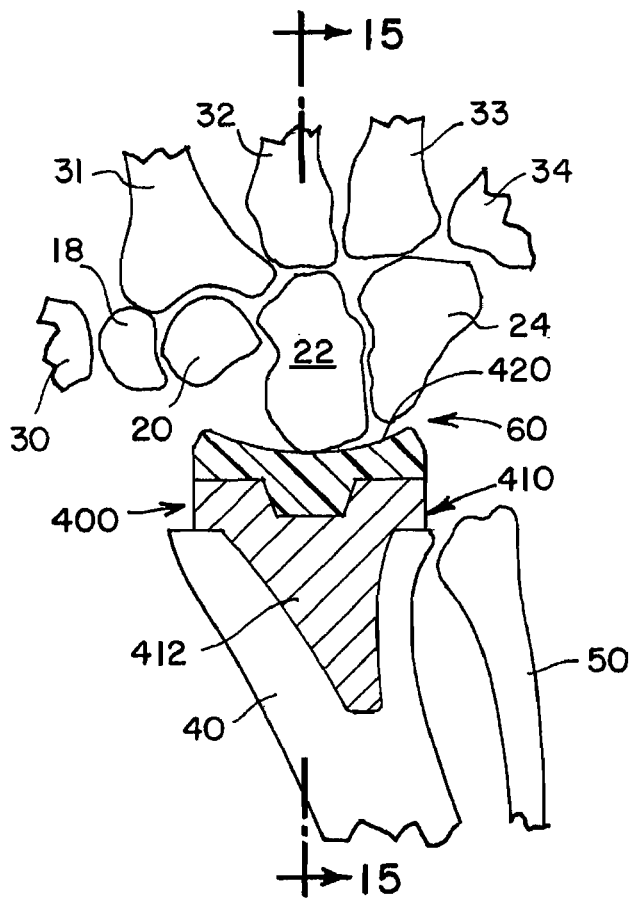
Figure 15:
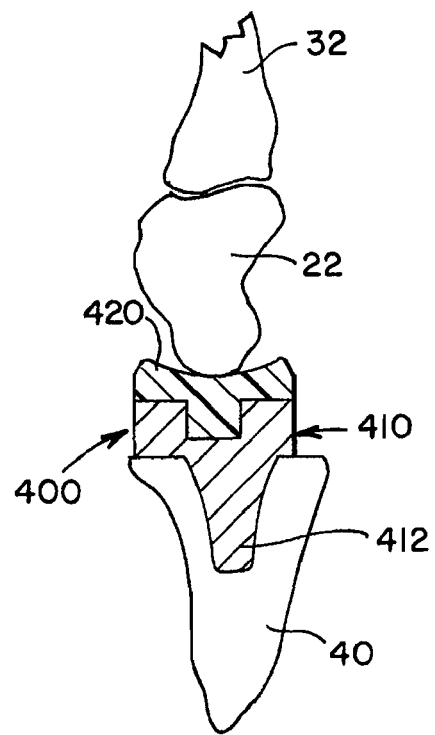
Figure 16:
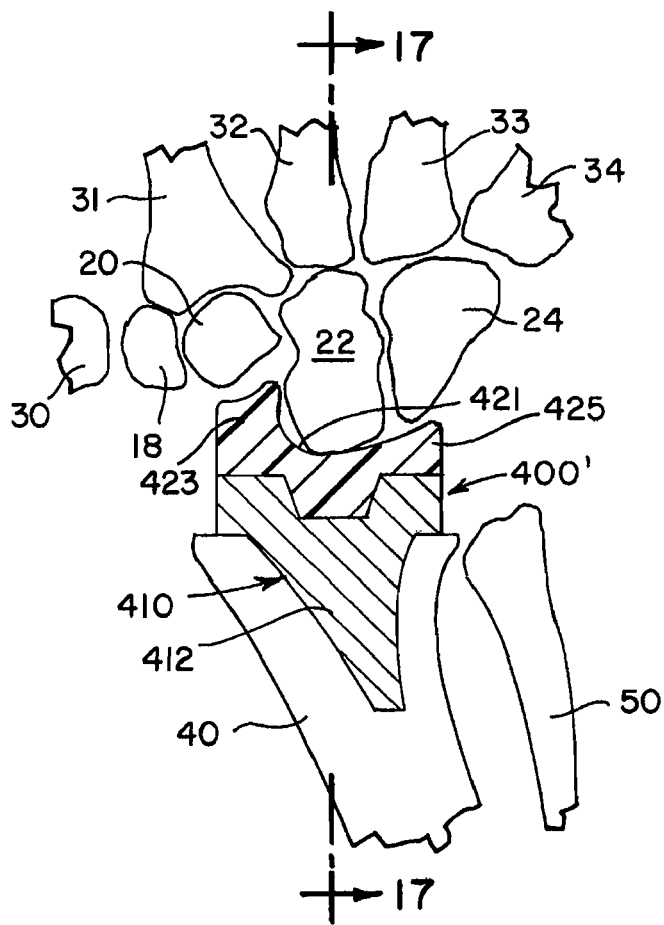
Figure 17:
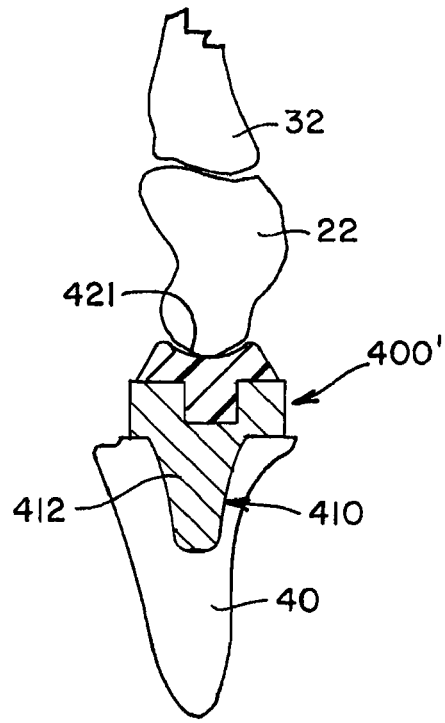

FIGS. 11A-C show an exemplary wrist implant according to another embodiment;

FIGS. 12 and 13 are cross-sectional dorsal views of a total wrist arthroplasty implant according to a second embodiment;

FIG. 14 is a cross-sectional dorsal view of a hemi-arthroplasty implant according to one embodiment installed in the right hand of a human patient;

FIG. 15 is a cross-sectional radial view taken along the line 15-15 of FIG. 14;

FIG. 16 is a cross-sectional dorsal view of a hemi-arthroplasty implant according to another embodiment installed in the right hand of a human patient; and FIG. 17 is a cross-sectional radial view taken along the line 17-17 of FIG. 16.

DETAILED DESCRIPTION OF PREFERRED EMBODIMENTS

As previously mentioned, wrist implants typically include two components, namely, a distal component (or carpal component) and a proximal component (or radial component). Typically, conventional wrist implants include a somewhat elliptical shaped convex distal component that articulates with a similarly shaped concave radial component (or vice-versa). While these designs readily allow rotations about the two major orthogonal axes, coinciding with classically and anatomically defined wrist motions of flexion-extension and radioulnar deviation, these designs do not readily permit wrist motions that are oblique to these orthogonal axes. As mentioned above, the dart thrower's motion is about an axis that is a combination of both flexion-extension and radial-ulnar deviation.

The implants and procedures described herein allow the patient to perform dart thrower's motion without restraint from the implant. It will be understood that the implant systems disclosed herein are applicable to coupled motion in a wrist; however, the present invention may be adapted to a number of other applications, including knee joints, elbow joints, or any other joints that require a wide variety of complex movements and/or their combination.

Figure 2:
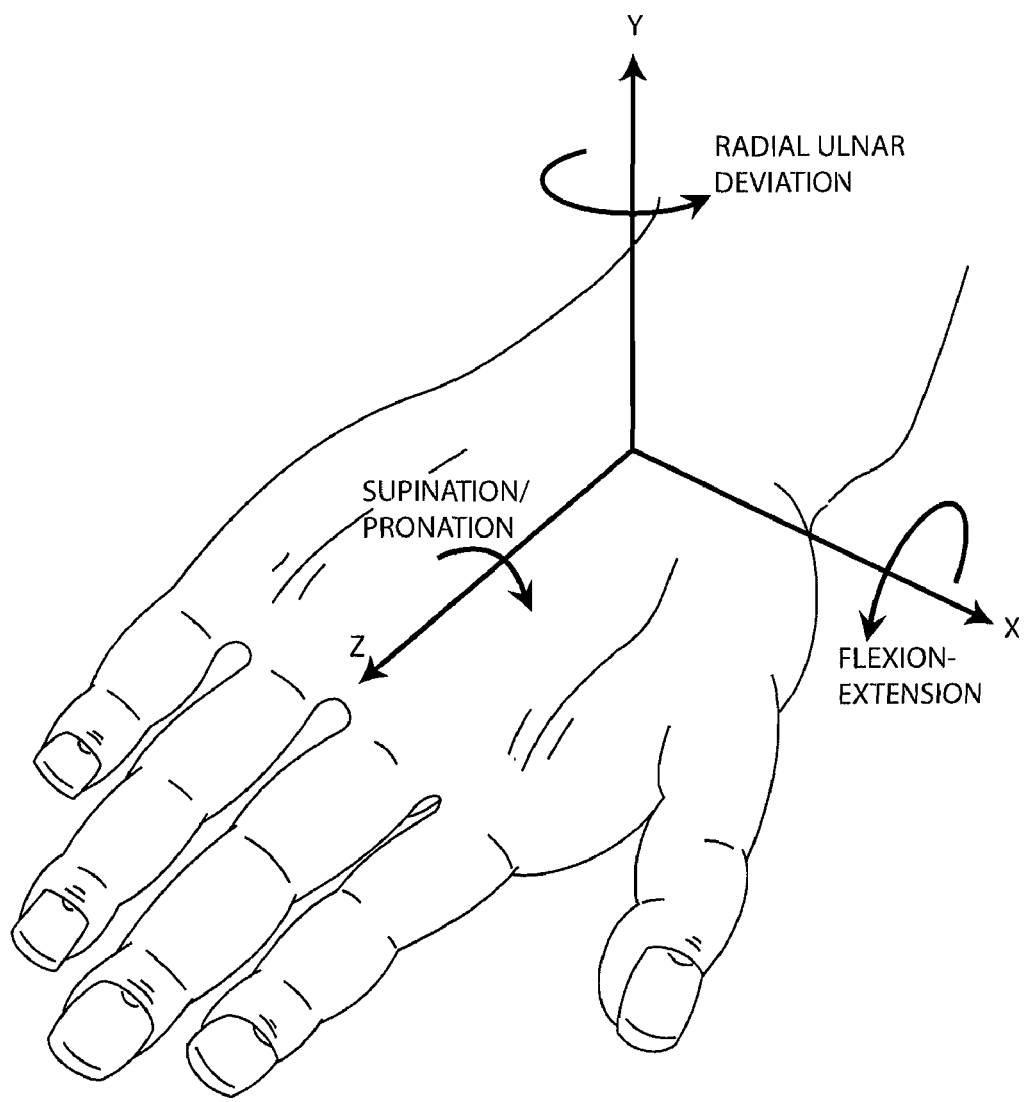
FIG. 2 illustrates a right-handed, orthogonal coordinate system for the right wrist, with the positive x-axis being in the radial direction, the positive y-axis being in the dorsal direction and the positive z-axis being in the distal direction.

While a standard ball-socket design, as opposed to an elliptical design, would fulfill the design requirement for permitting the dart thrower's motion, this design also readily permits unconstrained supination and pronation at the wrist (i.e., rotation about the z-axis in FIG. 2), a motion that does not physiologically occur in substantial amounts in the wrist but rather in the forearm at the distal radial ulnar joint and at the proximal radius.

Referring to FIGS. 3-8, a wrist implant system 100 according to one embodiment is illustrated. The wrist implant system 100 is configured to permit a normal range of motion of the wrist, including a dart thrower's motion, while constraining non-physiological wrist motion. The implant system 100 is constructed to include two principal articulating components, namely, a first articulating component 110 (e.g., a distal component) and a second articulating component 200 (e.g., a proximal component). As shown in the dorsal views of FIGS. 3 and 4, the first and second articulating components 110, 200 are configured to interact with one another and be coupled to one another. Each of the first and second articulating components 110, 200 has two articulating portions, namely, a primary articulating portion and a secondary articulating portion.

Figure 3:
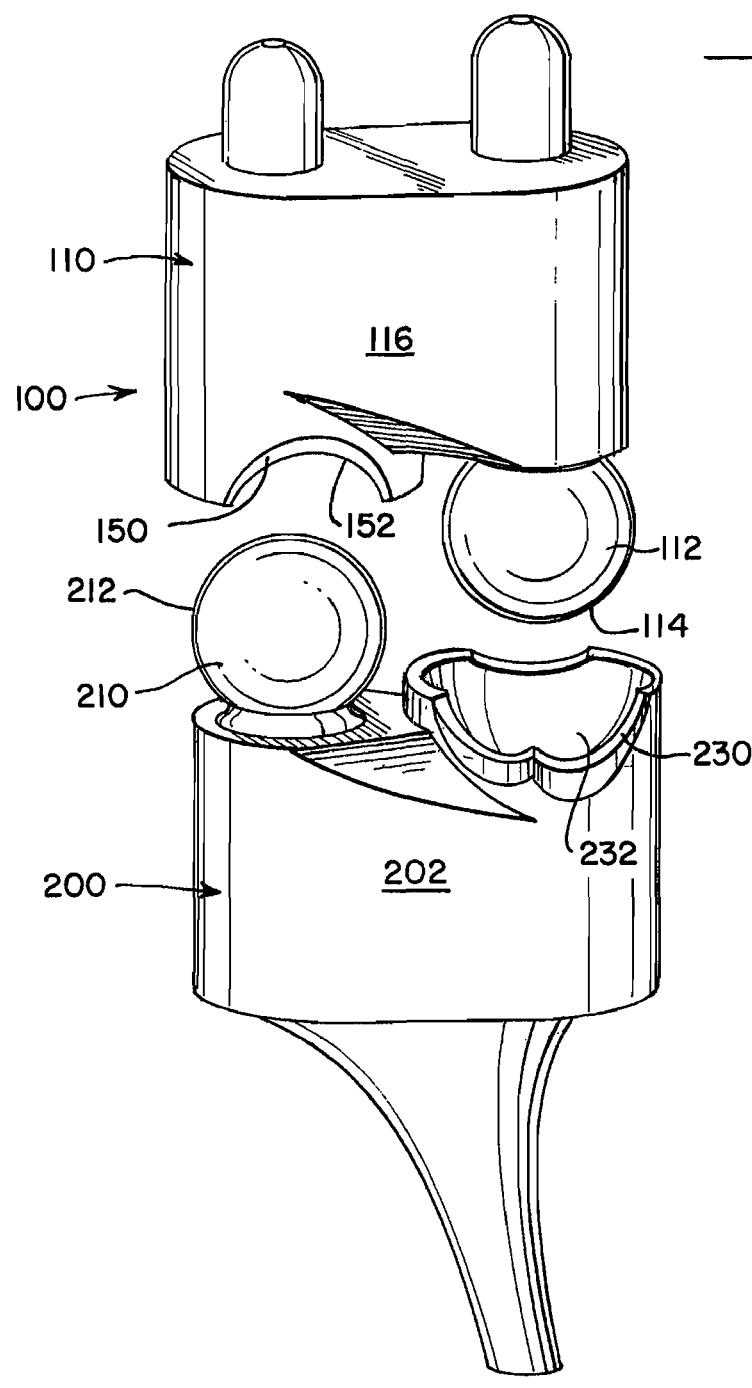
FIG. 3 is an exploded perspective dorsal view of an exemplary wrist implant according to one embodiment.

For example, the first articulating component 110 includes a primary articulating portion 112 and a secondary articulating portion 150. The first articulating component 110 can be formed as a single integral body that includes the primary articulating portion 112 in one location and the secondary articulating portion 150 in another location. The primary articulating portion 112 includes a surface 114 that is substantially curved or rounded outward. Alternatively, the primary articulating portion 112 can be configured to have a substantially convex shape. As shown in FIG. 3, the primary articulating portion 112 represents a projection or protrusion that extends outwardly from a base portion 116 of the first articulating component 110, with the portion 112 having the curved or convex shaped free end as described above.

The secondary articulating portion 150 is formed adjacent the projection that defines the primary articulating portion 112. The secondary articulating portion 150 is configured to include a surface 152 that is substantially curved or rounded inward. In some embodiments, the secondary articulating portion 150 can be thus configured to have a substantially concave shape.

The second articulating component 200 is configured to mate and interact with the articulating component 110. The second articulating component 200 can be formed as a single, integral part and includes a base portion (or a body) 202. In another embodiment the articulating components 100 and 200 may be constructed such that the subcomponents (e.g. 210, 112, 116, and 202) are modular. The second articulating component 200 includes a primary articulating portion 210 and a secondary articulating portion 230. The primary and secondary articulating portions 210, 230 are located adjacent one another. The primary articulating portion 210 is configured as a projection or protrusion that extends outwardly from the base 202 similar to how the primary articulating portion 110 extends outwardly from the base 116. The primary articulating portion 210 includes a surface 212 that is substantially curved or rounded outward. In some embodiments, the primary articulating portion 210 can be configured to have a convex shape, with the surface 212 being located at the free end of the protrusion that extends outwardly from the base 202.

The secondary articulating portion 230 includes a surface 232 that is substantially curved or rounded inward. In some embodiments, the secondary articulating portion 230 can be configured to have a concave shape.

Figure 4:
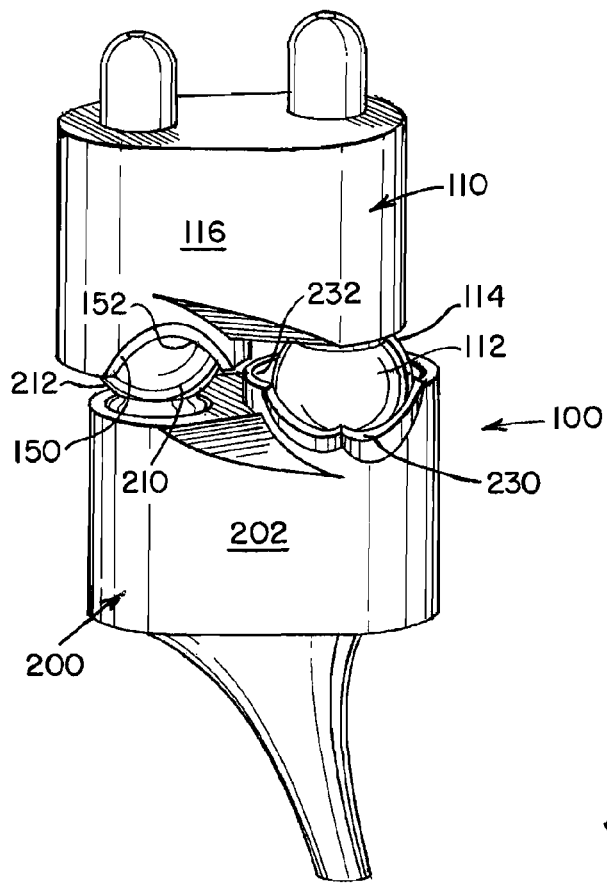
FIG. 4 illustrates the wrist joint implant of FIG. 3 with the carpal and radial components mated together.

In at least some embodiments, the surface 152 of the secondary articulating portion 150 of the articulating component 110 is configured to interact with and/or be in a substantially close proximity of the surface 212 of the primary articulating portion 210 when the components 110, 200 are brought in substantial proximity of each other, as shown in dorsal view of FIG. 4. When the components 110, 200 are brought in substantial proximity of each other, the surface 114 of the primary articulating portion 112 is also configured to interact with and/or be in a substantially close proximity of the surface 232 of the secondary articulating portion 230 of the second articulating component 200. It will therefore be appreciated that the surfaces 114, 152, 212, 252 are dimensioned relative to one another to allow for the above described interaction between the complementary surfaces of the two components 110, 200. This feature and the interaction/engagement between the two components 110, 200 are best shown in the dorsal views of FIGS. 3-4.

It will be appreciated that the dimensions of the two components 110, 200 can be such that the primary articulating portion 112 of the first articulating component 110 is configured to substantial fit within and/or be in a substantially close proximity of the secondary articulating portion 230 of the second articulating component 200 and the secondary articulating portion 150 of the first articulating component 110 is configured to substantially fit within and/or be in a substantially close proximity of the primary articulating portion 210 of the second articulating component 200.

The primary and secondary articulating portions can be shaped and positioned with respect to each other to permit the physiological motions of the wrist and limiting the non-physiological motions. For example, if one considers for reference the center of the primary 112 and the center of the secondary articular 150 portions, then these centers can be offset with respect to each other in a dorsal/volar direction. The axis defined by the two centers of the primary articulating portions defines the dart-thrower's axis and is orthogonal to the dart thrower's plane. In some embodiments, placement of a more radial articulating portion volar to the more ulnar articulating portion permits a motion about both the x and y axes of the anatomically defined coordinate system shown in FIG. 2.

In one embodiment and as shown in FIGS. 3-8, a double ball and socket design is provided as the means of articulation between the proximal component 110 and the distal articulating component 200. In this embodiment, the articulating surfaces of the components 110, 200 have spherical shapes and as described above, the component 110 includes the primary articulating portion 112 that has a spherical shape since it is in the form of a spherical ball and the secondary articulating portion 150 likewise has a spherical shape in that it is in the form of a concave recess (spherical socket). Similarly, the distal articulating component 200 has a spherical shape and includes the primary articulating portion 210 that has a spherical shape since it is in the form of a spherical ball and the secondary articulating portion 230 likewise has a spherical shape in that it is in the form of a concave recess (spherical socket). Accordingly, the components 110, 200 provide a double spherical ball and socket design with the components 110, 200 mating together by inserting one ball into one socket and inserting the other ball into the other socket.

In one embodiment, the geometrical center of the primary articulating portion 112 corresponds to the kinematic center of wrist in the proximal pole of the capitate bone. The secondary articulating portion is also somewhat spherical in shape and is located radially and volarly to the primary portion. The dimensions and locations of the secondary articulating portions are such that the proximal component 110 is configured to have a range of motions, such as translations, rotation (e.g., radial rotation), or any other complex or simple motion, as well as, any combination of these motions, about a predetermined location on the primary portions based on the range of wrist motions. Such predetermined location can be a center of the primary portion. The motions include: wrist flexion and extension, radial and ulnar deviation, and a range of coupled or dart thrower's motions. The location of the secondary articulating portions limits radial deviation relative to the other directions, limits inverse dart-thrower's motion, and constrains the amount of supination and pronation.

When the articulating portions of the wrist implant system are configured to be substantially spherical in shape, the primary convex portion 112 can be located at the geometrical center of the proximal pole of the capitate. The secondary concave portion 150 can be located radial and volar to the primary portion 112. The shape and location of the two portions readily permit wrist motion in normal physiological directions, while constraining non-physiological wrist motion.

In another embodiment, the primary and secondary convex articulating portions 112 and 210 may have a shape that is generally curved, not spherical or only partially spherical. It may also be advantageous to have the shape and size of the curved surface 112 differ from that of the curved shape of 210. The concave articulating portions 150 and 230 would be appropriately shaped to permit the proper mating between the components 110, 200.

Thus, according to one embodiment, each of the components 110, 200 has non-spherical primary and secondary articulating surfaces. In this embodiment, the primary articulating surface 112 and/or the secondary articulating surface 150 of the component 110 has a non-spherical shape that is complementary to the non-spherical shape of the primary and/or secondary surfaces 210, 230 of the component 200. The non-spherical articulating surfaces of the two components 110, 200 mate with another and provide the same advantages as the first embodiment in that the implant enables dart-throwing, restricts non-essential motions, moves the center of rotation distally and more closely replicates the shape and function of the midcarpal joint. It will be appreciated that the components 110, 200 in this embodiment can have any number of different shapes and sizes and in particular, the primary and secondary articulating surfaces can be shaped and sized based on the needs of patients.

Thus, while a design similar to a ball and socket is provided in this embodiment, the primary and secondary articulating surfaces that make up the "ball and socket" are not limited to having spherical shapes but instead, can have non-spherical shapes, including irregular shapes. Further, it is understood that a combination articular surface, comprised of a single ball and socket and an adjoining non-continuous ellipsoidal or asymmetrical surface may be utilized in this embodiment.

Figure 9:
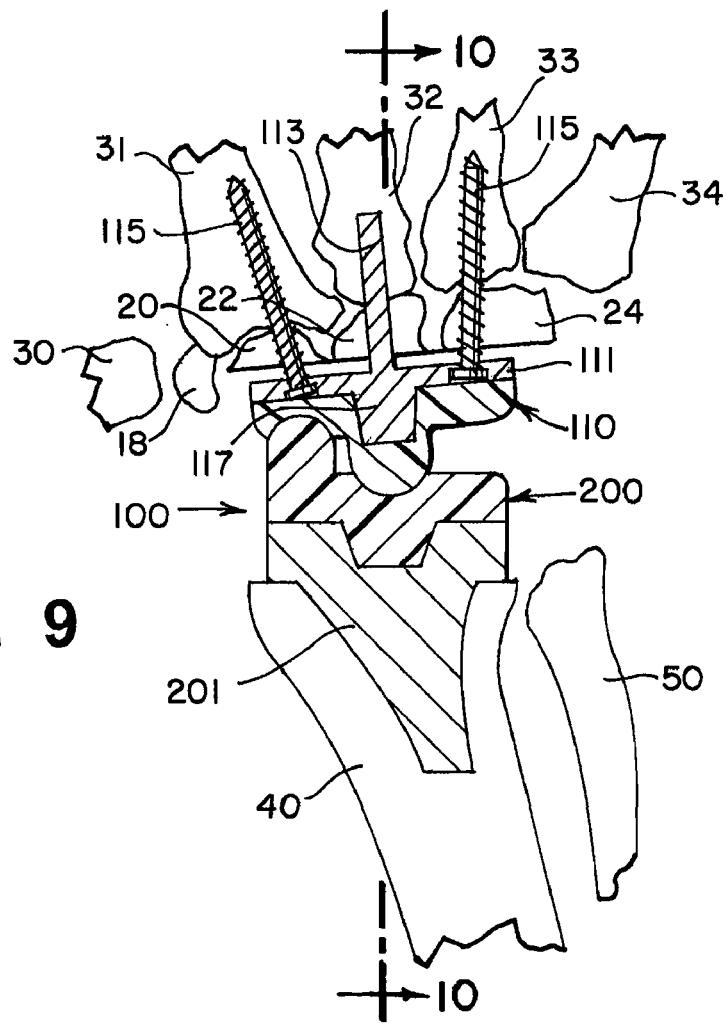
FIG. 9 is a cross-sectional dorsal view of the implant of FIG. 3 implanted into a wrist.

FIGS. 9 and 10 show the implant 100 installed in a wrist of a patient. In particular, the component 110 is coupled to a carpal plate 111 for attachment of the component 110 to the bones. For example, the carpal plate 111 can have some combination of fixed porous coated stems 113 and some combination of variable-angle locked or conventional screws to gain fixation on the metacarpal bones. The purpose of the variable-angle configuration is to maximize optimal direction of screw inclination with respect to the carpal plate 111, as might be necessitated in a revision situation or in certain diseases or post-traumatic situations that might have resulted in bone loss or deformity. The purpose of the "locked" screw system is to engage the screw into the plate 111 and improve implant fixation rigidity.

The carpal plate 111 can include a coupling component 117 that is configured to couple the component 110 to the plate 111. The coupling component 111 can be in the form of a protrusion or shank that has a Morse taper. As is known, a Morse taper refers to a taper of ⅝ths of an inch per foot. Preferably, the carpal plate 111 and any fixed stems 113 are coated with a porous material similar to the stem of the radius component 200.

In the embodiment shown in FIG. 9, a central stem 113 for insertion into one of the metacarpal bones is between two carpal screws 115 for fixation to two other metacarpal bones. Bone preparation prior to implant placement will result in fusion between the bones.

Similarly, the component 200 includes an integral stem portion 201 or it can be coupled to a stem portion 201 as shown in FIG. 9. More specifically, the component 200 can be in the form of a liner that is securely coupled to a stem portion 201 for attachment to the radius 40. As discussed herein, the components 110, 200 can have a modular aspect when they are in the form of liners in that the components 110, 200 can be separate from and removable from the other fixation components, such as the carpal plate 111, screws 113 and 115, and stem portion 201.

However, it will be appreciated that other ways of attaching the components 110, 200 of the wrist implant 100 to the wrist bones can be used.

Moreover, in one embodiment, one or more of the components 110, 200 can be constructed so that the concave surfaces thereof are formed of plastic, such as polyethylene, and the convex surfaces are formed of metal. This configuration offers improved wear properties and increases the life of the implant. As can be understood by one skilled in the art, other materials as well as other arrangements of the spherical surfaces of components 110, 200 are possible.

Figure 5:
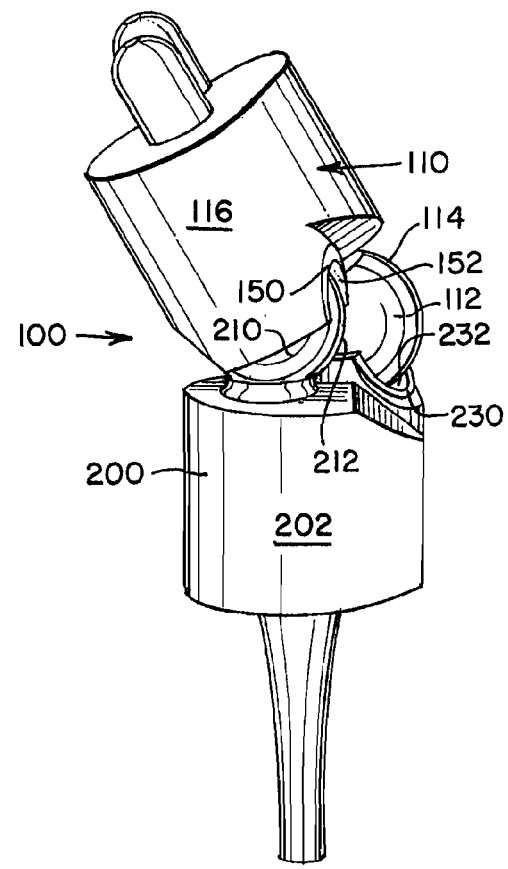
FIG. 5 is a radial perspective view of the implant of FIG. 3 at a degree of flexion.
Figure 6:
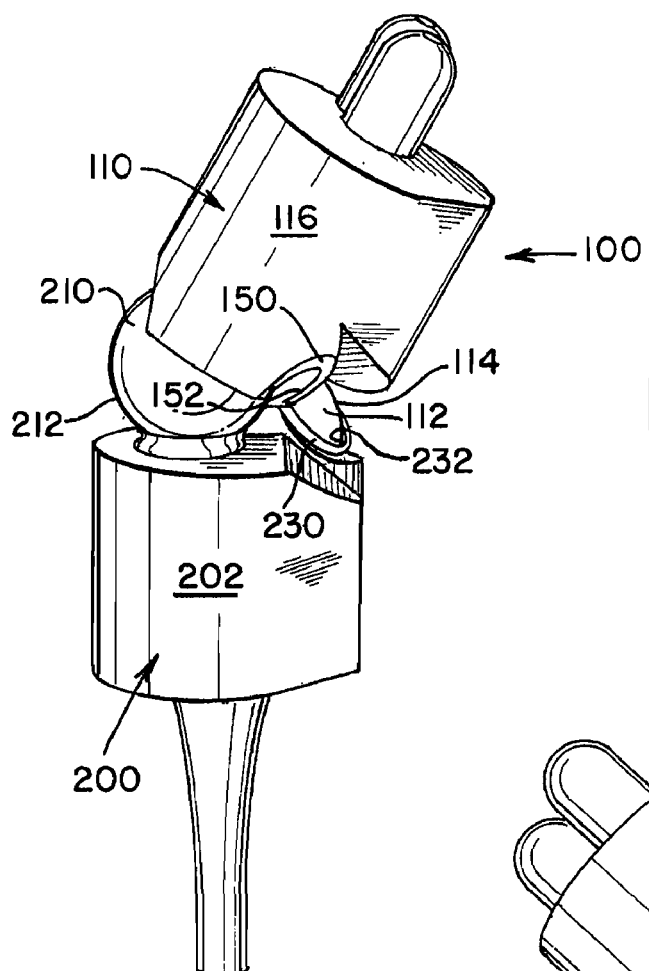
FIG. 6 is a side perspective view of the implant of FIG. 3 at a degree of extension.
Figure 7:
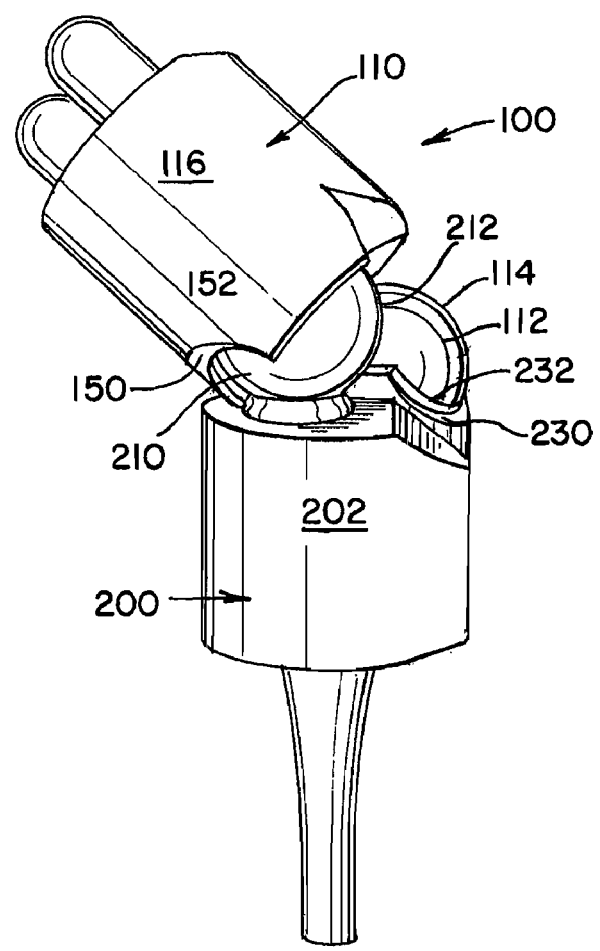
FIGS. 7 and 8 illustrate the implant of FIG. 3 as it moves in a dart thrower's motion.
Figure 8:
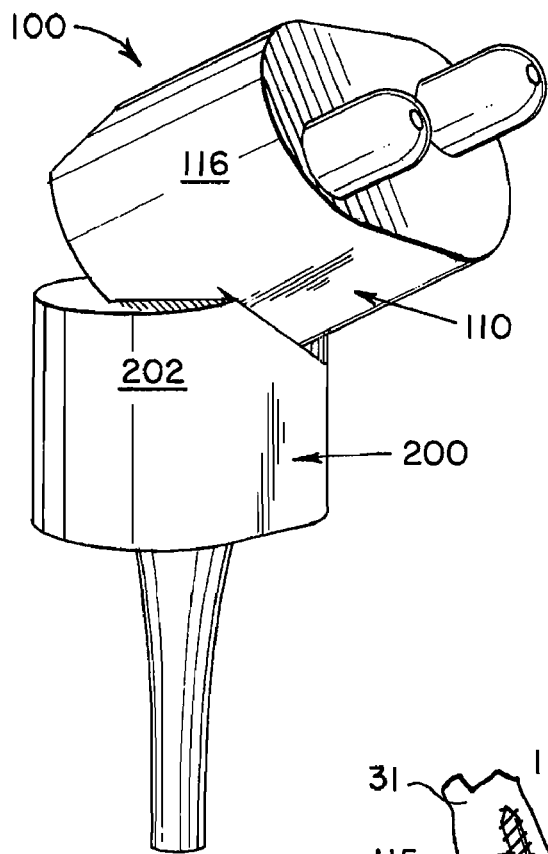

The exemplary wrist implant system illustrated in FIGS. 3-8 allows the patient or user of the implant system 100 a wide variety of motions. In particular, the implant system 100 allows the basic motions of flexion, extension, radial and ulnar deviation. Additionally, the implant system 100 allows a combination of these motions and coupled dart thrower's motions. These motions can be performed at varying angular displacements with regard to the x-y axis (shown in FIG. 2) as well as to each other. While conventional systems are incapable of performing dart-thrower's coupled motions, the present invention allows performance of such desired range of motions, when the axes of the motions are at varying degrees to each other (e.g., dart thrower's motion can be performed diagonally with respect to the flexion motion at an oblique angle). The implant system 100 is preferably configured so that is accommodates about 140 degrees of flexion/extension (70 degrees flexion and 70 degrees extension). FIG. 5 illustrates the implant system 100 at an exemplary degree of flexion; FIG. 6 illustrates the implant system 100 at an exemplary degree of extension; and FIGS. 7-8 show movements of the implant system 100 during a dart thrower's motion.

Moreover, the implant system 100 of the present invention also can be configured to constrain excessive motion(s) in certain directions, such as supination and pronation. Supination is a rotation of the hand and forearm so that the planar surface of the hand is facing upward. Pronation is a rotation of the hand and forearm so that the surface of the palm is facing downward. Because the articulating components 110, 200 include convex/concave shapes of their respective articulating portions, the components 110, 200 are configured to restrain certain movements of the components 110, 200 and allow other movements at the same time. Further, the juxtaposition of the components 110, 200 and surrounding ligamentous tension is such that the components 110, 200 are prevented from disengaging from each other once the implant system 100 is placed in the wrist.

The system 100 is advantageously designed so that the components 110, 200 interact with minimal friction over a range of motions of the implant system 100. This allows for smooth movements of the joints and provides for a long lifetime of the components 110, 200.

As will be appreciated, the implant system 100 of the present invention may be configured to be used in other bodily joints (e.g., finger, knee, elbow, shoulder, spine, ankle, foot, etc.). Accordingly, the implant system 100 can be dimensioned and constructed to fit a desired joint. The implant system 100 allows for any degrees of freedom with regard to the motions allowed by the components 110, 200, as well as, any angles of rotation, displacement, and/or other motions so long as such motions will not cause unnatural joint movements.

As shown in FIGS. 11A-C, one or more of the components 110, 200 can have primary and secondary articulating surfaces that are defined by a continuous or partially continuous, substantially smooth surface that closely replicates the anatomic surfaces of the midcarpal joint as described herein. In other words, the surface of the convex articulating portion 112 can be continuous or partially continuous with the concave articulating surface 152 of the first component 110 and similarly, the convex articulating surface 212 can be continuous or partially continuous with the concave articulating surface 232 of the second component 200. It will be appreciated that FIGS. 11A-C are intended to show the articulating liner portions of the implant and do not completely show the means, e.g., fasteners, for fixing the liners to the respective bones.

In another embodiment of the present invention that is illustrated in FIGS. 12-13, an implant system 300 that includes a first component 310 and a second component 320. The implant system 300 is configured to replicate the articular surface of the midcarpal joint of the normal wrist, and as such, enable the dart-thrower's functional arc of motion. In this embodiment, one or more of the components (310, 320) can have primary and secondary articulating surfaces that are defined by a continuous or partially continuous, substantially smooth undulating surface that closely replicates the anatomic surfaces of the midcarpal joint. One or both of the components (310, 320) can have an undulating convex/concave articular shape and the components (310, 320) are oriented with respect to one another so that the complementary and oppositely shaped articulating surface portions mate with one another to permit the implant to articulate over the wide range of desired motions discussed above. In other words, the proximal or radial component liner can contain a primary concave surface and a distal and volar secondary articular convex surface and a reciprocal distal or carpal component.

In the case of a total wrist arthroplasty, the first component 310 is in the form of a carpal component and the second component 320 is in the form of a radial component. As described below, the carpal component 310 is fixed to the metacarpals and the radius component 320 is fixed to the radius 40. It will be understood that FIGS. 12 and 13 show the carpal bones in their entirety; however, when the first component 310 is implanted in the manner described below, proximal portions of select carpal bones (e.g., trapezoid 20, capitate 22, and hamate 24) will be removed as shown in FIGS. 9 and 10. The carpal bones are shown in their entirety in FIGS. 12 and 13 in order to illustrate how the implant 300 replicates the center of rotation of the capitate 22.

The radial component 320 includes a stem portion 322 and an articulating component that is formed of a base or block portion 324 that is formed at one end of the stem portion 322 and a polymeric portion (articulating surface) 326. The block portion 324 is formed of a metal material and serves as a metal backing for the polymeric portion 326 which can be formed of a polyethylene material, preferably ultra-high molecular weight polyethylene. This metal backed articulating surface of the radial component 320 is constructed to simulate the shape of the normal midcarpal joint (i.e., distal scaphoid-lunate-triquetral). The stem portion 322 is typically a porous coated structure.

The carpal component 310 includes a carpal plate 330 and an articulating undulating convex and concave surface 340 that is coupled to the carpal plate 330. Similar to the carpal plate 111 (FIG. 9), the carpal plate 330 can have some combination of fixed porous coated stems 332 and some combination of variable-angle locked or conventional screws to gain fixation on the metacarpal bones. In the embodiment shown in FIG. 12, a central stem 332 for insertion into one of the metacarpal bones is between two carpal screws 334 for fixation to two other metacarpal bones. The primary convex articulating surface of the carpal component 340 articulates with the radial component 320 and is rigidly fixed to the carpal plate 330. The secondary convex articulating surface of the carpal component is volar and radial to the primary articulating surface. The primary articulating surface 340 has an elliptical shape and in particular, is formed to have a shape that replicates the normal capitate-hamate articular surface and is a modular component in that it is designed to be press fitted onto the carpal plate 330. The carpal plate 330 can include a coupling component 331 (similar to component 117 of FIG. 9) that is configured to couple the modular carpal ball 340 to the plate 330.

Advantageously and different from current prosthetic designs, the center of rotation of the joint in each of the embodiments disclosed herein will be distal to the radial articular surface, approximating the normal center of rotation in the capitate (see reference character "A" in FIG. 12). The implant's articulating surface will be unique, replicating the midcarpal rather than the radiocarpal articular surface. The major axis of motion of the wrist implant 300 is advantageously in the dart thrower's functional arc of motion (radial extension to volar flexion) rather than traditional orthogonal axes of flexion-extension and radial-ulnar deviation. This is achieved by using a carpal component primary articulating surface 340 having an elliptical shape (capitate-hamate shaped) with its axis oriented such that the dart thrower's motion is enabled.

The implant system 300 is accordingly and advantageously a modular system that enables alteration of the relative constraint of the implant depending on the etiology of the particular disease condition that is being remedied (e.g., inflammatory vs. degenerative vs. post-traumatic). The modular restraint is generally shown by reference character "R" in FIG. 12. In one embodiment, the polymeric portion 326 can include a labrum or "buildup" that is present circumferentially for providing added restraint. The use of a labrum finds particular utility in patients that are afflicted with rheumatoid arthritis, lupus arthritis, or other inflammatory conditions that may lead to ligament and capsular laxity. In patients with post-traumatic arthritis or other conditions without inherent ligament instability, the implant can be placed without the labrum.

The total wrist implant system 100 and 300 thus offers the following advantages and features: (1) a primary convex articulation that corresponds in shape and orientation to the native capitate-hamate joint; (2) a modular shape and a degree of constraint according to a particular disease condition; (3) a more distal "anatomic" center of motion in the center of capitate head relative to a radial implant component; (4) an articulating surface that enables a smooth dart thrower's axis of motion by minimizing implant constraint in this plane (dart thrower's motion plane); (5) a more physiologic primary axis of motion in the dart-thrower's plane that decreases implant-bone interface stresses and prolongs durability of the component fixation; and (6) variable-angle locking screws in the carpal plate that further increase implant fixation, (7) a design that does not constrain normal kinematics of the wrist during functional activities, and (8) a distal and volar, secondary articulating convex surface that constrains certain undesirable motions (e.g., inverse dart-thrower's motion and supination-pronation).

FIG. 12 illustrates the above-mentioned articulating surface 326 that has an undulating convex and concave surface. In particular, the surface 326 has a concave articulating portion 329 and an adjacent convex articulating portion 327. Due to the undulating nature of the surface 326, the convex articulating portion 327 is in the form of a protrusion that extends upwardly from the concave articulating portion 329. The liner 340 (convex and concave articulating surface) of the carpal component 310 can include a concave portion 341 that is shaped and sized relative to the convex articulating portion 327. More specifically, the convex articulating portion 327 articulates with the concave portion 341 when the two liners of the implant mate with one another.

FIG. 13 illustrates a wrist implant 300' that is similar to wrist implant 300 of FIG. 12. FIG. 13 illustrates the modularity of the implant in that the articulating surface component 326 (a liner) can be carefully selected, installed, and changed based on the needs of a particular patient. In particular, the construction and orientation of wrist bones varies from patient to patient and therefore, one particular liner that offers the necessary range of motions, as well as the necessary degree of constraint, for one patient may not be suitable for another patient. The solution is to provide multiple liners that can easily be selected and installed and later removed if the patient's needs change.

FIG. 13 illustrates an articulating surface component 326' (liner) that includes concave articulating portion 329' and convex articulating portion 327' so as to form the above-described undulating convex and concave surface. The surface characteristics and shapes of the convex and concave portions 327', 329' are different than the shapes of the convex and concave portions 327, 329 and have been carefully designed and selected in view of the specific requirements of a particular patient. Once the proper articulating surface component is chosen, it is coupled to the stem portion 322.

In yet another embodiment, a hemi-arthroplasty implant for a joint (e.g., a midcarpal joint in the wrist) is provided and illustrated in FIGS. 14-15.

Figure 1:
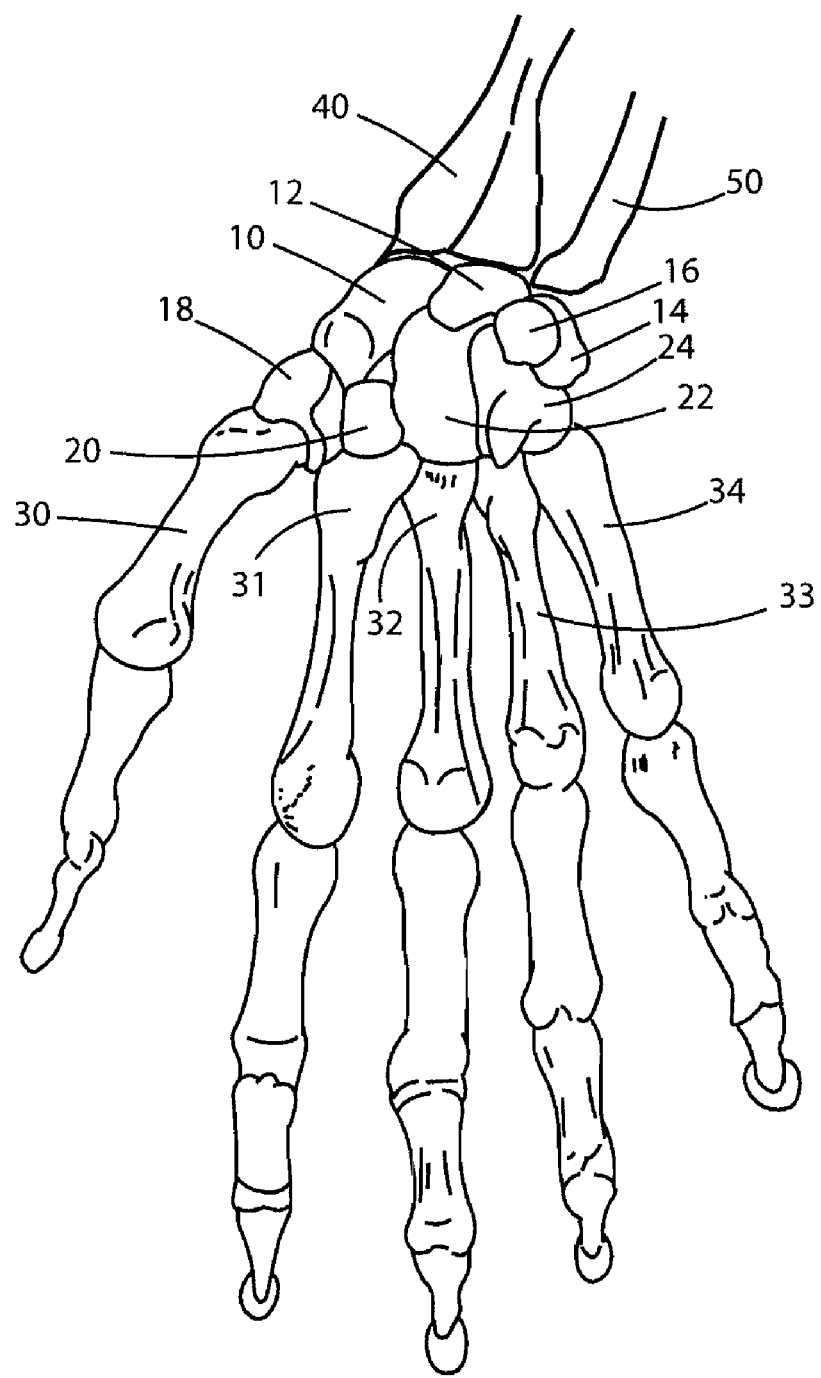
FIG. 1 is a palmar view of the bones of a human hand and wrist.

As previously mentioned, FIG. 1 illustrates a palmar view of the carpal bones of a right hand of a human. FIG. 14 is a dorsal view of the carpal bones of a right hand of a human with a hemi-arthroplasty implant 400 according to one exemplary embodiment being installed in the hand/wrist.

The hemi-arthroplasty implant 400 is particular suited for early stages of post-traumatic and osteo-arthritis of the radiocarpal joint. Arthritis resulting from an old injury of the scaphoid is commonly referred to as a SNAC wrist ("scaphoid non-union advanced collapse"), while arthritis resulting from a neglected scapho-lunate ligament injury is commonly referred to as a SLAC wrist ("scapho-lunate advanced collapse"). Both SNAC and SLAC wrists are the most frequent causes for wrist salvage reconstructions through partial or complete wrist fusion or proximal row carpectomy.

The installation of the hemi-arthroplasty implant 400 in the wrist of a patient involves a replacement of exclusively the proximal carpal row (scaphoid 10, lunate 12, triquetrum 14, and pisiform 16) (FIG. 1) and the distal radial articular surface, while at the same time, preserving the distal carpal row and its native articular surface, as well as the distal radio-ulnar joint (generally indicated at 60 in FIG. 14). The hemi-arthroplasty implant 400 includes a prosthesis 410 that is implanted in the radius 40. The prosthesis 410 includes a stem portion 412 which is implanted in the radius 40 in identical fashion as for the total wrist arthroplasty as by reaming a hole in the radius 40 and for robustness and rigidity, the stem portion 412 is typically formed of a metal material. The prosthesis 410 further includes a modular bearing surface 420 that can be formed of either a metal material, a ceramic, or a plastic material, such as polyethylene or polyurethane, or a pyrolytic carbon material, and is constructed to provide an articulating surface that functions in an optimal fashion when articulating with healthy articular cartilage of the native distal carpal row bones.

In the illustrated embodiment, the native capitate 22 and hamate 24 are preserved and articulate with the prosthesis 410 and more specifically, the articulating surface (modular bearing surface 420) resembles the native midcarpal joint (e.g., a radio-scapho-lunate fusion). As mentioned above, the distal radio-ulnar joint 60 is generally preserved, unless the surgeon should elect to remove it for treatment of concomitant degenerative arthritis of the distal radio-ulnar joint. More particularly and as shown in FIGS. 14 and 15, the modular bearing surface 420, which can also be referred to as a liner, has multiple concave surface portions as shown in FIGS. 14 and 15, including in the dorsal to palmar direction.

It will be appreciated that the configuration of the hemi-arthroplasty implant is similar to the radial component of the total wrist implant embodiment discussed above and in doing so, the surgeon has the option of replacing all or half of the wrist, and also the option of returning at another time to replace the distal component if so needed without changing the proximal fixation. The surgeon would simply change the articulating surface (liner) of the proximal component at the time of implantation of a distal component and conversion to total wrist arthroplasty. The articulating surface of the radial component can be formed of polyethylene in the total wrist implant design and formed of polyethylene, ceramic or pyrolytic carbon in the hemi-arthroplasty design. In the later, the shape-in liner may have a slightly more constrained shape, or might need a labrum or build-up as needed; however, these decisions are left to the surgeon's discretion and therefore, therefore the implant is truly modular in nature.

The concavity of the bearing surface 420 shown in FIGS. 14 and 15 serves to cradle the native capitate 22 so as to provide a replacement midcarpal joint that mimics a normal healthy joint. In other words, the curvature of the bearing surface 420 preserves the curvature of the midcarpal joint and maintains the curvature of the midcarpal space as shown in FIGS. 14 and 15 due to the configuration of the bearing surface 420. By configuring the bearing surface 420 to preserve the shape of the midcarpal joint, the patient is allowed to maintain the "dart-thrower's functional arc of motion."

FIGS. 16 and 17 illustrate a hemi-arthroplasty implant 400' that is similar to the hemi-arthroplasty implant 400 of FIGS. 14 and 15 with the exception that the modular bearing surface is different and is generally indicated at 421. Unlike the modular bearing surface 420 of the implant 400 which has a more uniform shape, the modular bearing surface 421 of the implant 400' has a more pronounced convex and concave undulating shape. The modular bearing surface 421 can be formed of either a metal material, a ceramic, or a plastic material, such as polyethylene or polyurethane, or a pyrolytic carbon material and is constructed to provide an articulating surface that functions in an optimal fashion when articulating with healthy articular cartilage of the native distal carpal row bones.

As with the embodiment of FIGS. 14-15, the native capitate 22 and hamate 24 are preserved and articulate with the prosthesis 410 and more specifically, the articulating surface (modular bearing surface 421) resembles the native midcarpal joint. As mentioned above, the distal radio-ulnar joint is generally preserved, unless the surgeon should elect to remove it for treatment of concomitant degenerative arthritis of the distal radio-ulnar joint. More particularly and as shown in FIGS. 12 and 13, the modular bearing surface 421, which can also be referred to as a liner, has multiple concave surfaces in that, as shown in FIG. 16, there is a concave surface in the dorsal to palmar direction, and as shown in FIG. 17, there is a concave surface in the two sides of the surface 421 and therefore, there is a degree of concavity in the side to side direction.

Unlike the embodiment of FIGS. 14-15, the modular bearing surface 421 has an enlarged concave section 423 as shown in the dorsal to palmar direction of FIG. 16. The enlarged concave section 423 has a height that is greater than an opposite section 425 and is configured to increase the articulation with the capitate 22 and also provide a convex articulation with the trapezoid and trapezium. In other words, the convex section 423 extends in a region between the trapezoid 20 and the capitate 22. The opposite section 425 is disposed proximate the interface between the hamate 24 and the triquetrum 14. The surgeon may choose to use this more constrained liner for diseases or situations (revision, capsular deficiency) that require a greater degree of constraint.

While exemplary drawings and specific embodiments of the present invention have been described and illustrated, it is to be understood that the scope of the present invention is not to be limited to the particular embodiments discussed. Thus, the embodiments shall be regarded as illustrative rather than restrictive, and it should be understood that variations may be made in those embodiments by workers skilled in the art without departing from the scope of the present invention as set forth in the claims that follow, and equivalents thereof. In addition, the features of the different claims set forth below may be combined in various ways in further accordance with the present invention.

What is claimed is:

1. A human wrist implant comprising:
   (a) a carpal component; and
   (b) a radial component;
   wherein each of the carpal and radial components comprises a primary articulating portion having a substantially convex surface and a secondary articulating portion having a substantially concave surface, the primary and secondary articulating portion of each component being continuous or partially continuous to one another;
   further wherein, when the carpal and radial components are in substantial proximity to each other, the convex surface of the primary articulating portion of the carpal component articulates with the concave surface of the secondary articulating component of the radial component, and the convex surface of the primary articulating portion of the radial component articulates with the concave surface of the secondary articulating portion of the carpal component.

2. The wrist implant system of claim 1, wherein the secondary articulating portion is configured to be radially and volarly disposed in relation to the primary articulating portion.

3. The wrist implant system of claim 1, wherein the primary and secondary articulating portions are configured to have different sizes.

4. The wrist implant system of claim 1, wherein each primary articulating portion of each of the distal and proximal components is configured to have a geometrical center that is configured to correspond to at least one of the geometric and kinematic centers of the wrist within the proximal pole of the capitate bone.

5. The wrist implant system of claim 1, wherein the secondary articulating portion of each of the distal and proximal components is configured to move about a predetermined location of each of the primary articulating portions based on a range of wrist movements.

6. The wrist implant system of claim 5, wherein the predetermined location is a center of the primary articulating portion.

7. The wrist implant system of claim 5, wherein the range of movements includes at least one movement selected from the group consisting of flexion/extension, radial and ulnar deviation.

8. The wrist implant system of claim 5, wherein the wrist implant is configured for a coupling of motion that progresses from some amount of wrist extension and radial deviation to some amount of wrist flexion and ulnar deviation.

9. The wrist implant system of claim 5, wherein the movement includes any combination or degree of coupling of flexion-extension and radioulnar deviation.

10. The wrist implant system of claim 1, wherein the secondary articulating portions are configured to limit non-physiological motions.

11. The wrist implant system of claim 10, wherein the non-physiological motions includes extreme radioulnar deviation and extreme flexion-extension.

12. The wrist implant system of claim 1, wherein the secondary articulating portions are configured to limit extremes of supination of the wrist, pronation of the wrist or both.

13. A human wrist implant comprising:
 a first component having a first protrusion with a convex shape and a first recessed portion with a concave shape; and
 a second component having a second protrusion with a convex shape and a second recessed portion with a concave shape,
 the concave shape of the first recessed portion being configured to accommodate the convex shape of the second protrusion and the concave shape of the second recessed portion being configured to accommodate the convex shape of the first protrusion such that the first and second components mate with one another to permit motion of the wrist in at least one physiological direction and constrain motion of the wrist in at least one non-physiological direction.

14. The wrist implant of claim 13, wherein each of the first protrusion and second recessed portion is configured to have a geometrical center that is configured to correspond to at least one of the kinematic and geometrical centers of the wrist within the proximal pole of the capitate.

15. The wrist implant of claim 13, wherein the first and second components are configured to permit movement about a predetermined location of each of the first and second protrusions based on a range of wrist movements.

16. The wrist implant of claim 15, wherein the predetermined location is a center of each of the first and second protrusions.

17. The wrist implant of claim 15, wherein the wrist implant is configured for a coupling of motion that progresses from some amount of wrist extension and radial deviation to some amount of wrist flexion and ulnar deviation.

18. The wrist implant of claim 15, wherein each of the first and second recessed portions is configured to limit radial deviation.

19. The wrist implant of claim 15, wherein the first and second recessed portions are configured to constrain supination and pronation of the wrist.

20. A wrist implant configured to replicate a midcarpal joint of a human, said wrist implant comprising:
 (a) a first component configured to be attached to metacarpal bones and comprising
  a first part that has a convex shape and replicates a normal or diseased midcarpal surface of the capitate and hamate, and
  a carpal plate configured to be fixed to the metacarpal bones and to which the first part is detachably coupled to define a modular system; and
 (b) a second component configured to be attached to the radius bone and comprising an articulating surface constructed to simulate the proximal shape of the midcarpal joint and mate with the first part
 wherein the modularity of the implant permits different degrees of constraint or motions between the first and second components to be selected according to a particular disease condition.

21. The wrist implant of claim 20, wherein a substantially concave primary articulation is provided between the first and second components that simulates the normal midcarpal joint in shape and orientation, and is continuous with a substantially convex secondary articulation that is radial and volar to the primary articulation.

22. The wrist implant of claim 20, wherein a major motion of the wrist implant is orientated in a radial extension to ulnar flexion functional arc of motion.

23. The wrist implant of claim 20, wherein an axis of an articulating surface of the first part is oriented so as to enable a coupling of motion that progresses from some amount of wrist extension and radial deviation to some amount of wrist flexion and ulnar deviation.

24. The wrist implant of claim 20, wherein the each of the first and second components is in the form of a liner that is configured to be attached to a respective plate.

* * * * *